(12) United States Patent
Koljaka et al.

(10) Patent No.: US 10,568,637 B2
(45) Date of Patent: Feb. 25, 2020

(54) SURGICAL SAW

(71) Applicant: Cutting Edge Medical LLC, Louisville, KY (US)

(72) Inventors: Franc Koljaka, Branford, CT (US); Vasiliy Abramov, Louisville, KY (US)

(*) Notice: Subject to any disclaimer, the term of this patent is extended or adjusted under 35 U.S.C. 154(b) by 669 days.

(21) Appl. No.: 15/256,856

(22) Filed: Sep. 6, 2016

(65) Prior Publication Data
US 2018/0064447 A1    Mar. 8, 2018

(51) Int. Cl.
*A61B 17/14* (2006.01)
(52) U.S. Cl.
CPC .................. *A61B 17/142* (2016.11)
(58) Field of Classification Search
CPC ..... A61B 17/14; A61B 17/142; A61B 17/144; A61B 17/1637
See application file for complete search history.

(56) References Cited

U.S. PATENT DOCUMENTS

| | | | | |
|---|---|---|---|---|
| 4,513,742 A * | 4/1985 | Arnegger | ............. | B23D 61/006 30/350 |
| 4,784,034 A * | 11/1988 | Stones | ................. | B23D 61/121 30/292 |
| 8,672,943 B2 * | 3/2014 | Fisher | ................. | A61B 17/142 606/82 |
| 2006/0272468 A1 * | 12/2006 | Gupta | ................. | B23D 61/006 83/835 |

* cited by examiner

*Primary Examiner* — Anu Ramana (57) ABSTRACT

A sagittal surgical saw blade consisting of a planar body having side edges, a proximal end for attachment to an oscillatory power device and a distal end defining a cutting head carrying distally extending spaced apart teeth. The teeth are configured to provide a kerf wider than the thickness of the cutting head. A large chip collection void is formed in the cutting head and the sides of the body define left and right chip collection and evacuation areas.

10 Claims, 5 Drawing Sheets

SURGICAL SAW

FIELD OF THE INVENTION

This invention relates generally to surgical saw blades. More particularly, this invention relates to a sagittal surgical saw blade that, when actuated, is relatively stable and allows a higher cutting speed with minimal temperature build up.

BACKGROUND OF THE INVENTION

Surgical procedures often require the bone and cartilage be cut for removal or for doing a repair procedure. Commonly such procedures employ a power saw which may be reciprocating or oscillating. Oscillating power saws are preferred since the cutting rate is faster than with reciprocating saws.

A major problem with oscillating saws is the removal of bone chips created during the cutting procedure. The buildup of bone chips will produce friction resulting in excessive heat at the cutting area. Temperature above 47° C. for more than 1 minute have been shown to severely damage bone tissue and care must be taken to minimize the temperature at the cutting area. In addition bone chips can jam the movement of the blade resulting in a reduction of cutting efficiency and can produce "chattering" of the blade making accuracy of the cut difficult. Saw blades have been designed to aid in chip removal in an attempt to minimize temperature buildup but such blade designs have been only partially successful.

Accordingly, it is an object of the invention to provide an improved sagittal surgical saw blade for use in surgical procedures.

Another object of the invention is to provide an improved sagittal surgical saw blade that removes chips of material in an efficient manner.

Yet another object is to provide a sagittal surgical saw blade having an improved cutting rate.

Still yet another object of the invention is to provide an improved sagittal surgical saw blade that creates less heat buildup during use than the prior art sagittal saw blades.

These and other objects and advantages of the present invention will become apparent from the following description of the invention taken in conjunction with the drawings

SUMMARY OF THE INVENTION

The present invention relates to an improved sagittal surgical saw blade for use with an oscillating power device. The improved sagittal surgical saw blade has a higher cutting rate and improved removal of bone chips over a leading prior art saw blade. This results in less time for the cutting procedure and a lower rate of temperature buildup as compared to the prior art blade. This benefits both the surgeon and the patient in that a cutting procedure can be accomplished in less time and there is a lower chance of bone damage due to temperature buildup. Bone chip removal is efficient so that there is little blade jamming and blade chattering making the cutting procedure more accurate and easier for the surgeon to carry out.

The improved sagittal surgical saw blade comprises a planar body defining an upper and a lower surface. The improved sagittal surgical saw blade has a proximal end adapted for attachment to a power drive device and a distal cutting end carrying spaced apart teeth that are configured to create a kerf or cutting line that is wider than the thickness of the planar body. The distal end portion of the planar body defines a neck portion that is narrower than the rest of the body. The sides of the body at the distal end portion proximally flare out from the neck to form shoulders on the planar body and flare out distally to the cutting edge of the blade and define a distal cutting head and form void area on each side of the body that extends from the shoulders to the cutting edge. Preferably a void is also formed in the portion of the area of the planar body between the cutting edge and the neck portion.

The teeth are spaced from adjacent teeth a distance of about 0.5 tooth width to about 1.5 of the tooth width. The spacing between the teeth serves as an collection point for bone chips for early removal of the chips from the cutting area. Also, since there are fewer teeth contacting bone during the cutting process there is less friction and less vibration resulting in an increase in overall stability of the blade.

To produce a cutting line or kerf that is wider than the thickness of at least the cutting head of the blade, the cutting points of the teeth of the blade may be biased outwardly with respect to the plane of the body of the blade. Adjacent teeth are biased in opposite directions. In this manner the cutting contact area between the teeth and the bone is minimized and the kerf produced by the blade is wider than the thickness of the body of the blade. Alternatively, the surfaces of the blade at least at the cutting head may be ground from the original thickness leaving the teeth unground. In this manner a wider kerf is created and space is formed between the upper and lower surfaces of at least the cutting head and the material being cut to facilitate chip removal.

DESCRIPTION OF THE PRIOR ART REFERENCE BLADE

Figure 1:
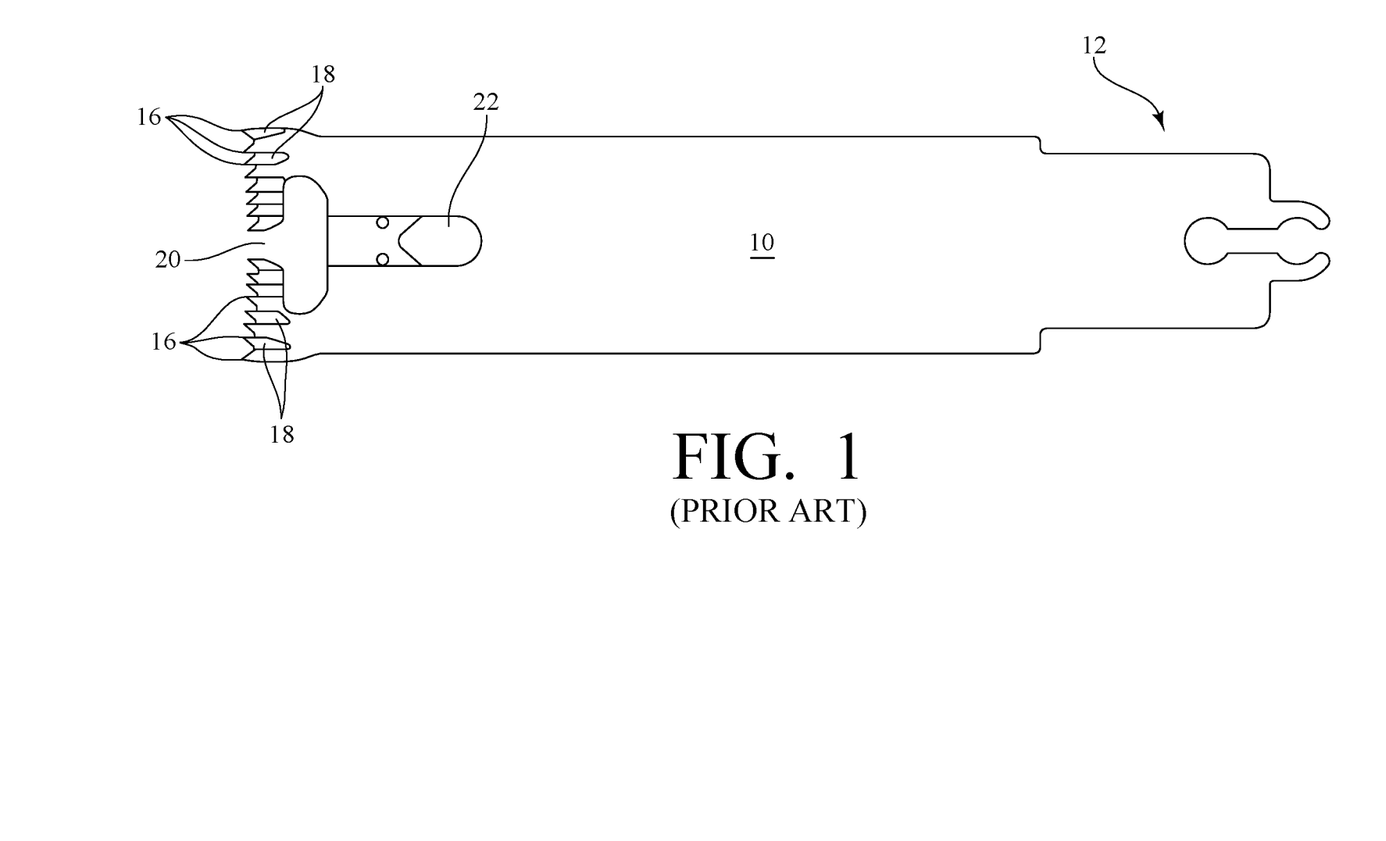
FIG. 1 is a plan view of a leading prior art sagittal saw blade used as a reference.

Referring to FIG. 1 a reference blade distributed by a leading distributor of medical devices is illustrated. The blade is more completely described in U.S. Pat. No. 8,216,262 granted Jul. 10, 2012 in the name of Denis O'Donoghue and assigned to Stryker Ireland, Ltd.

The blade consists of a planar body 10 of uniform thickness having a proximal end 12 and a distal end 14. The proximal end 12 is configured to facilitate coupling the blade 10 to a power source (not shown) to provide oscillatory motion to the blade. The distal end 14 is provided with spaced apart triangularly shaped teeth 16, the apex of which defines the cutting edge of the blade 10. A first void 20 in the body 10 opens to the cutting edge and a second void 22 is formed in the body proximally of the first void. Indentations 18 are formed between the teeth 16 and extend proximally from the teeth. Depending on their location along the cutting edge the indentations are tapered so their depths decrease proximally and are at their minimum at the side of the body 10, the planar surface of the body or open into the first void 20. As the blade oscillates the bone chips are forced into the first void and through the indentations 18 to the side of the body 10 or to the first void 20 or to the planar surface of the body.

Description of the Preferred Embodiment

Figure 2:
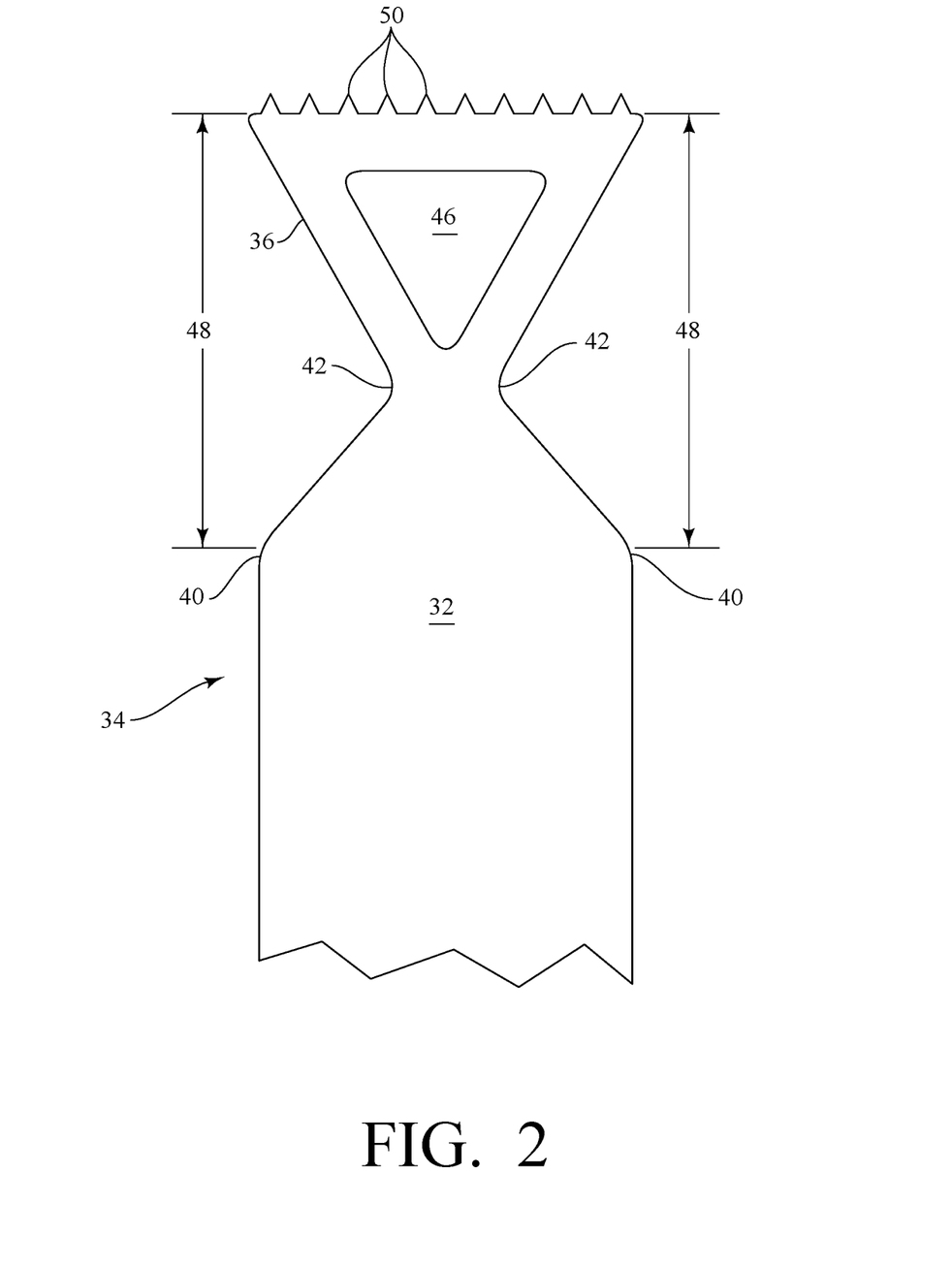
FIG. 2 is a plane view of a sagittal surgical saw blade with the proximal portion cut away and illustrating the distal cutting portion according to one embodiment of the invention.

FIG. 2 is a plan view cut away to show the distal portion 34 of a sagittal surgical saw blade 30 in accordance with the invention. The inventive sagittal surgical saw blade 30 comprises a rectangular planar blade body 32 of uniform thickness having upper and lower surfaces, side edges, opposed proximal and distal end edges and a longitudinal axis extending therebetween. The blade body 32 further defining a distal portion 34 and a proximal portion (not shown) that may be configured in a number of ways for attachment to a oscillatory power device (not shown) depending on the type of power device used to impart oscillatory motion to the distal end of the saw blade 30. The configuration of the proximal end and the manner of attaching it to a power device is not within the scope of the present invention.

A distally extending cutting head 36 is formed on the distal portion 34 by the side edges of the distal portion 34 of the planar body 32 sloping distally inwardly towards the longitudinal axis to form a shoulder 40 and a neck 42 and then sloping distally outwardly from the neck to a cutting edge 38 at the distal end of the cutting head. The width of the cutting edge 38 may be equal to, greater than or smaller than the width of the planar body 32 at the shoulder 40. Thus for working in a confined area a small cutting edge 38 may be most desirable while working in a more unconfined area a wider cutting edge may be desired for faster cutting speed.

A void 46 in the cutting head 36 is provided to assist in capturing and removing bone chips from the cutting edge 38. The void 46 extends proximately from adjacent the cutting edge to approximately the neck 42. Preferably the void 46 defines an inverted triangle to conform to the general shape of the cutting head 36. The void 46 is significantly large and represents about 43% of the area of the distal 35 mm of the blade body 32. The strength of the blade 30, normally formed of stainless steel, is not affected by the large void 46. It will be understood however, that should the blade 30 be formed from a different material the size of the void 46 may be adjusted depending on the strength of the material forming the blade.

Likewise the area on each side of the cutting head 36 between the left and right end of the cutting edge 38 and the left and right shoulders 40 forms a left and right collection and containment space 48 for bone chips.

Figure 3:
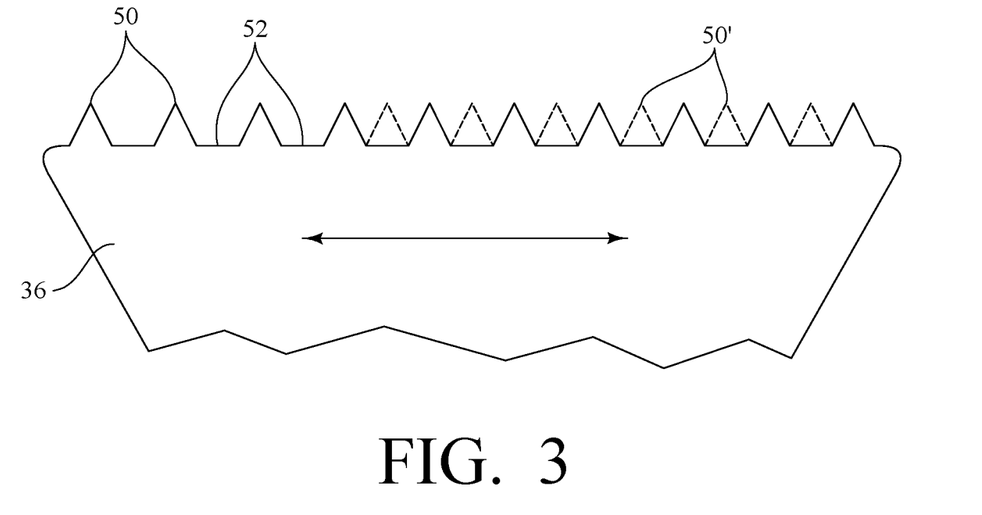
FIG. 3 is a plan view partially cut away for compactness of illustration of the distal cutting end of the sagittal surgical saw blade of FIG. 2.

A series of triangularly shaped teeth 50 are disposed along the cutting edge 36 and extend distally therefrom. As most clearly shown in FIG. 3 the teeth 50 are spaced apart to define a gap 52 therebetween. The gap 52 may be as small as one half of the width of the teeth 50 at their bases to about one and a half base width of the teeth. A preferred gap 50 is about one base width and is illustrated in FIG. 3 by phantom teeth that would be normally present as adjacent teeth in a conventional saw blade cutting edge. Rather than positioning the teeth 50 immediately adjacent one another, which is conventional, the larger gap between teeth provides space for receiving bone chips and helps to remove them from interfering with the cutting action of the blade.

Figure 4A:
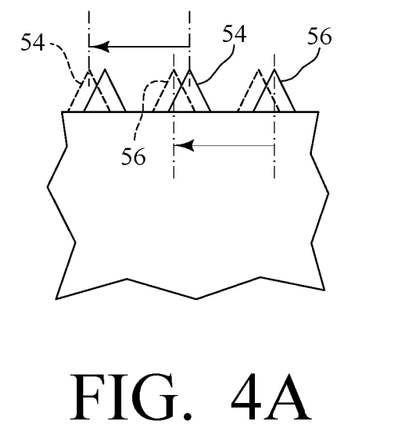
FIG. 4A is a portion of the cutting edge partially cut away for compactness of illustration showing the overlapping path of travel of adjacent teeth of the sagittal saw blade to the left and FIG. 4B illustrates the overlapping path of travel of adjacent teeth to the right during oscillatory movement of the blade.
Figure 4B:
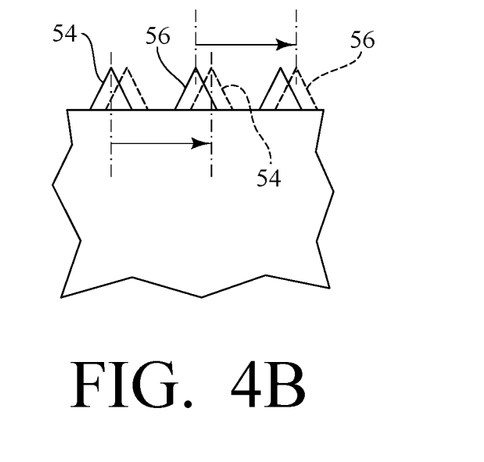

Depending on the length of the oscillation travel path, the gap 52 should not be so large that the travel path of a tooth 50 cannot overlap a portion of the travel path of an adjacent tooth. This is most clearly illustrated in FIGS. 4A and 4B a portion of a cutting edge 38 which carries a first tooth 54 and a spaced adjacent second tooth 56. As shown the oscillation path is between the left side of the figure and the right side. As the blade oscillates to the right tooth 54 and 56 likewise travel to the right. At the terminus of the oscillatory path to the right tooth 54, shown in phantom, in its rightmost position slightly overlaps the position tooth 56 occupied at the start of oscillation. Likewise, oscillation to the left moves tooth 56, shown in phantom, to a position slightly to the left of the position tooth 54 occupied. In this manner there are no gaps in the cutting action of spaced apart adjacent teeth 50 and a continuous kerf is produced.

Figure 5A:
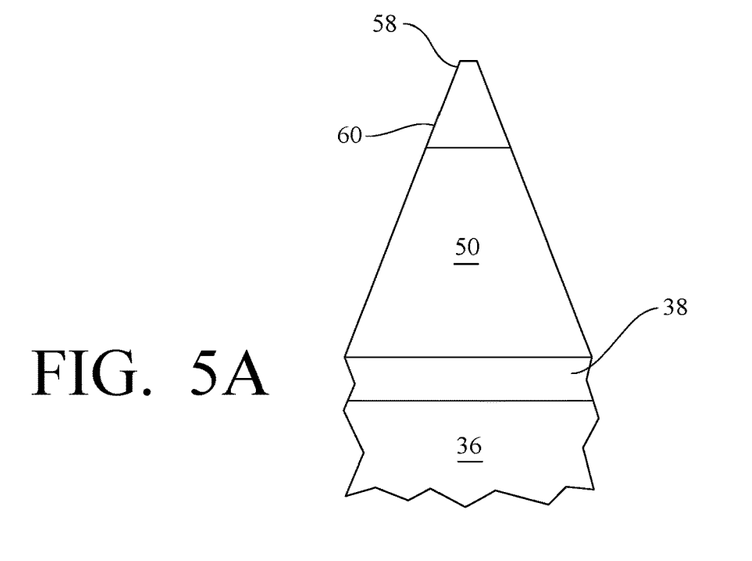
FIG. 5A is a side view of a tooth of the sagittal surgical saw of FIG. 2 and FIGS. 5B, 6A and 6B are enlarged end views of the teeth of the sagittal surgical saw of FIG. 2 illustrating alternate ways in which the cutting points of the teeth are configured to produce a wider kerf.

FIG. 5A is an enlarged side view of a distally extending triangular tooth 50 carried at the cutting edge 38 of the sagittal surgical saw blade of the invention. The apex of the triangular tooth 50 defines the point 58 of the tooth.

Figure 5B:
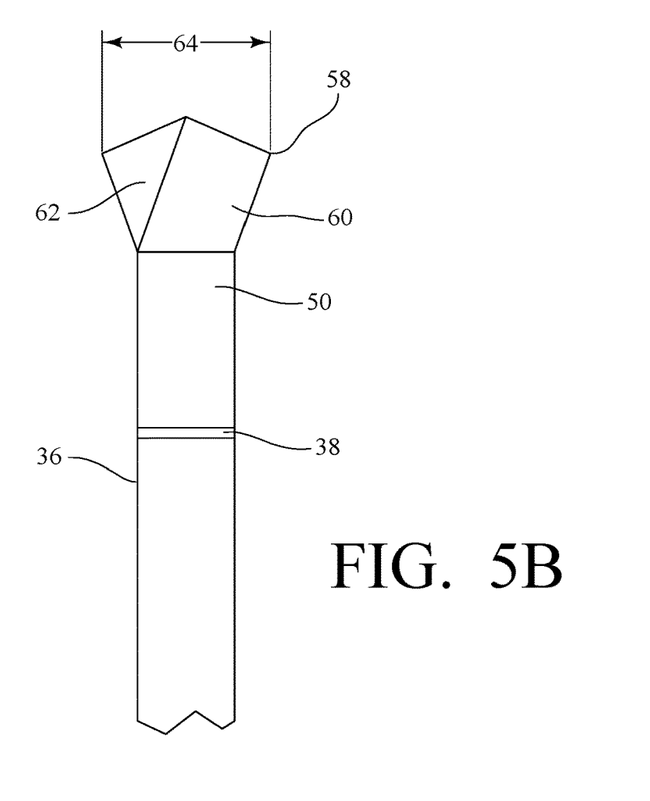
Figure 6A:
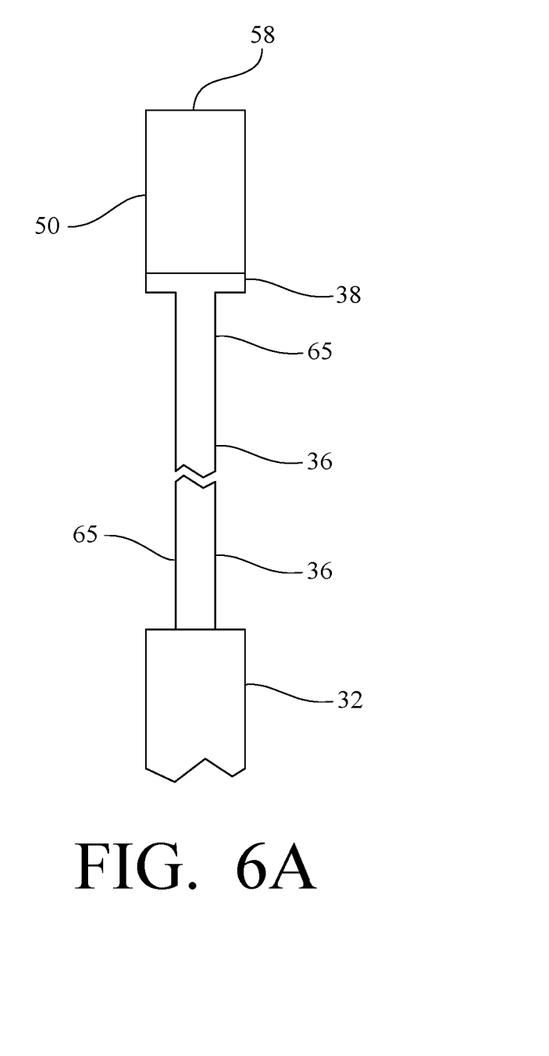
Figure 6B:
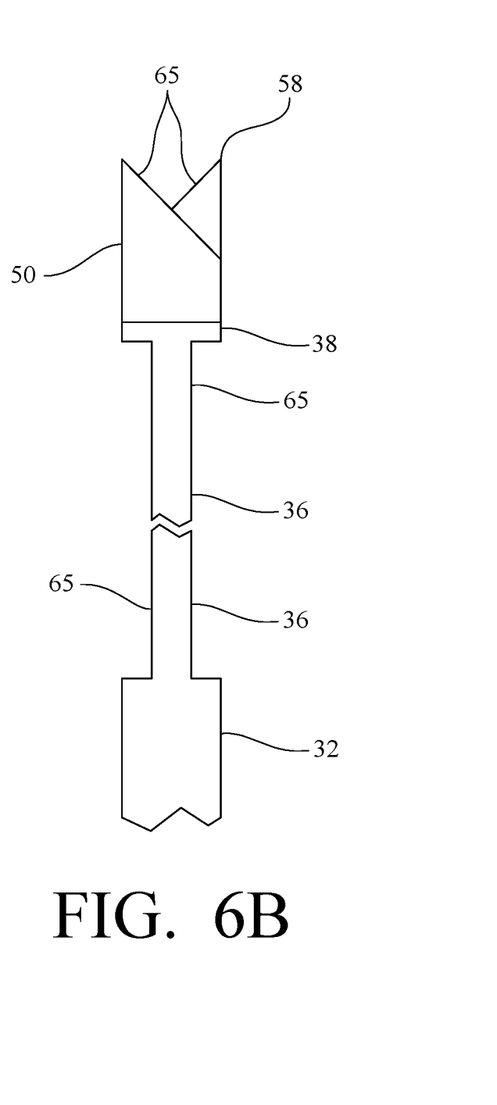

FIG. 5B is an end view of the tooth 50 of FIG. 1. A portion 60 of the tooth 50 proximal to the point 58 is biased with respect to the plane of the cutting head 36 while the portion 62 of the adjacent tooth is biased with respect to the plane of the cutting head in the opposite direction. All the teeth 50 are alternately biased in the fashion to create a contact line 64 that produces a cutting line or kerf that is wider than the thickness of the surgical sagittal saw blade. The biased portions 60 of the teeth 50 may be formed by deforming a portion of each tooth adjacent the point 58. In another embodiment, illustrated by FIG. 6A, at least the distal portion 34 of the body 32 is ground at surfaces 65 while the teeth are unground so that the thickness of at least the cutting head 36 is less than the cutting edge 38 and teeth 50. Preferably, the cutting action of the teeth of FIG. 6A is improved by also grinding alternate surfaces 65 of each tooth 50 as shown by FIG. 6B to provide a biased surfaces similar to FIG. 5B. With the kerf of the sagittal surgical saw blade being wider than the thickness of at least the distal portion of blade body. Contact between the surface of the blade body and the material being cut is minimized and space for removal of cutting chips is provided to reduce friction and improve cutting speed.

Test Procedures and Results

To demonstrate the effectiveness of each improved feature of the surgical sagittal saw blade of the invention, larger tooth gap, large void 46 in the cutting head and the body configuration to provide space 48 on each side of the blade for collection of bone chips, and biasing the portion 60 of the teeth 50, each feature was tested individually using a leading sagittal surgical saw blade. Stryker System 6, of the type shown in FIG. 1 as a reference. This blade is one of the most widely used products in the surgical practice.

More than 10 testing sets with competition products and variations of the new proposed designs have been performed with the goal to reach a combination of the lowest temperature and the fastest speed possible. The cutting tests were performed on a cast PMMA square rod 1"×1". PMMA is a material used in the medical field with physical and thermal properties very similar to the human bone and has been widely used as testing material in the research and development of medical devices. The temperature of the cutting area was measured with a digital thermometer through two type K thermocouples inserted at the center of the rod and at a distance of 3 mm from the cutting line. The temperature-time functions were recorded on a PC communicating serially with the thermometer. The temperature increase from room temperature was measured as the average of multiple (3-5) cutting tests for both thermocouples. The cutting time was also measured and converted to cutting speed for better comprehension.

Test 1—Tooth Gap

Sample blades, referred to Blade 1, had a solid planar body with no gaps or voids. The test blades having only more widely spaced teeth as shown and described in connection with FIGS. 2-3 were produced and tested against the reference blades as shown in FIG. 1. The spacing between the teeth of the test blades was slightly greater than one tooth width at the base. The spacing between the teeth of the reference blade was equal to the width of the proximal extending indentations formed between each tooth. The results are set forth in Table 1 below.

TABLE 1

| Blade Model | Cutting Speed | Temperature Increase |
| --- | --- | --- |
| Reference Blade | 16.1 mm/min | 72.2° c. |
| Test Blade 1 | 19.3 mm/min | 70.6° C. |

The cutting speed shows an increase of 20% while the temperature difference is only 2% lower (within the margin of error). Increasing the distance between the teeth creates more space for the chips and allows the blade to advance faster which can explain the higher cutting speed. On the other hand, since the sample tested here was a full solid blade without any gaps, the larger contact surface area between the material, cutting chips and the blade itself result in more friction and, as consequence, more heat generation.

Test 2—Effect of Collection Spaces

Test blades, referred to as blade 2, consisted of a planar body configured as illustrated and described in connection with FIG. 2. The teeth 50 were arranged as for a standard blade with the tooth bases being adjacent to one another so that there was little or no gap between adjacent teeth. The configuration of the blade body provided a large void 46 in the cutting head 36 and side collection spaces 48 as shown in FIG. 2. The total void area in the first 35 mm length of the reference blade represents a little more than 9% of the total area while in the proposed design is about 43% (center and sides). The tests have shown that the strength of a hardened stainless steel blade is not affected at all from this modification. The results are shown in Table 2.

TABLE 2

| Blade Model | Cutting Speed | Temperature Increase |
| --- | --- | --- |
| Reference Blade | 16.1 mm/min | 72.2° c. |
| Test Blade 2 | 19.6 mm/min | 73.8° C. |

It will be seen from the results of test 1 and test 2 is that while there is an increase in cutting speed there is very little improvement in temperature increase during the cutting operation. It appears that the chips created during the cutting process remain entrapped for longer times in the cutting area and there is no way for them to freely move away from the cutting area. The thickness of the blade body is uniform along all the blade length and in close contact with the material being cut. Material chips that are not pushed sideways have to force their way proximally down the cutting head 36 in order to reach the large void 46 or the side collection areas 48. This produces an increase of the friction between the blade and the material resulting in more heat generation and higher temperatures. For this reason, while the cutting speed increases in both cases by about 20%, the temperature difference is not significantly improved compared to the reference blade.

Test 3 Effect of Widening the Kerf

The test blades, identified as test blade 3, consisted of a planar body with no void in the body and no side collection spaces and little or no spacing between the teeth bases. The points of the teeth were alternately offset to provide a cutting line or kerf that is wider than the thickness of the planar body of the blade. Test blades 3 were compared against reference blades. The results of the comparison are set forth in table 3.

TABLE 3

| Blade Model | Cutting Speed | Temperature Increase |
| --- | --- | --- |
| Reference Blade | 16.1 mm/min | 72.2° c. |
| Test Blade 3 | 21.3 mm/min | 63.1° C. |

By offsetting the teeth in the manner described to create a kerf that is wider than the thickness of the body of the blade there is created a space between the blade body and the material being cut and contact between the blade body and the material is minimized and friction substantially reduced. Cutting speed is increased by 32% and temperature rise difference is reduced by about 13%.

Test 4 Effect of Combining the Features of Test Blades 1-3

Test blades identified as test blade 4 were produced in accordance with the invention and compared to the reference blade of FIG. 1. The bodies of test blades 4 were configured as illustrated in FIG. 2 to include a large void 46 in the cutting head 36 and side spaces 48 defined between the shoulder 40 and the distal end of the cutting head. The spacing between the teeth 50 was equivalent to one tooth width at the base. The points of the teeth 50 were alternately offset with respect to the plane of the body to create a kerf that is wider than the thickness of the blade body. The results are set forth in table 4 below.

TABLE 4

| Blade Model | Cutting Rate | Temperature Increase |
| --- | --- | --- |
| Reference Blade | 16.1 mm/min | 72.2° c. |
| Test Blade 4 | 26.5 mm/min | 55.3° C. |

The test results show that the cutting rate for the blades incorporating the features of the invention are substantially greater than for the reference blade or the test blades 1-3. The increase in cutting rate reduces the time a cutting procedure requires and thus increasing the efficiency of a surgical procedure that requires a bone to be cut. Table 5 presents in tabular form the cutting rates and percent improvement for the all the test blades as compared to the reference blade.

TABLE 5

| Blade Model & Feature | Cutting Rate | % Improvement |
| --- | --- | --- |
| Reference Blade | 16.1 mm/min | — |
| Test Blade 11 Tooth Space | 19.3 mm/min | 20% |
| Test Blade 2/Void at Cutting | 19.6 mm/min | 22% |

TABLE 5-continued

| Blade Model & Feature | Cutting Rate | % Improvement |
| --- | --- | --- |
| Head & Side collection spaces Test Blade 3/Kerf wider than body thickness | 21.3 mm/min | 32% |
| Improved Blade/includes all features | 26.5 mm/min | 65% |

With the new and improved blade design cutting speed is 65% higher and the temperature increase from room temperature is 23% lower than the reference blade. These test results also confirm that the benefits of the combination of the new features are much higher that the designs with only one of the proposed improvements.

Although it is not fully understood it appears that the larger space between the teeth provides a first quick relief to the large amount of chips created during the cutting process, permitting to the blade to advance continuously without interference from bone chips. The space between the blade and the material surface created by the teeth offset resulting in a wider kerf makes it possible for the chips to move out of the cutting area to the blade side surfaces. The large gaps at the center and the sides of the blades allow the chips to be entirely removed out of the area and, additionally, reduce the friction between the blade and the material.

The maximum temperature created by the novel sagittal surgical saw blade of the present invention was on average 17° C. below the reference blade which is the actual top product in the market. Combined with a 65% higher cutting speed, the time period at the maximum temperature will be shorter than with the reference blade. The risk of osteonecrosis is thus diminished with obvious benefits not only for the patient, but for the surgeon, too, since it reduces the risk of subsequent corrective interventions.

It is also noted that with the improved sagittal surgical saw blade, the novel blade exhibited significantly less vibration. Due to the high efficiency of removal of material chips the novel blades advanced with a steady pace through the material being cut and chattering and jamming of the blade did not occur. The operator noted that with the blade of the invention there was less hand fatigue because of less vibration.

From the foregoing drawings and text there is provided and improved sagittal surgical saw blade incorporating features that singularly provide little improvement over the prior art but when combined in the manner described unexpectedly results in a sagittal surgical saw blade vastly improved over the prior art. The invention has been disclosed in terms of the preferred embodiment that fulfills the objects set forth above.

Various changes and modifications from the teachings of the present invention may occur or be contemplated by those skilled in the art without departing from the spirit and scope of the invention. Accordingly, it is intended that that the present invention be limited only by the terms of the appended claims.

What is claimed is:

1. A sagittal surgical saw blade comprising:
   a. comprising a planar blade body having side edges and opposed proximal and distal end edges, upper and lower surfaces, opposed proximal and distal end portions and a longitudinal axis extending between said proximal and distal end edges, said proximal end portion adapted for attachment of said blade body to an oscillatory drive mechanism;
   b. said side edges at said distal end portion of said blade body sloping distally inwardly towards said longitudinal axis of said blade body to form a neck and then outwardly to form left and right shoulders in said blade body,
   c. a cutting head being formed by said side edges sloping distally outwardly from said neck to said distal end edge, said distal end edge defining the cutting edge of said blade;
   d. an area on each side of said cutting head between left and right ends of the cutting edge and each of said left and right shoulders, respectively, defining a left and a right collection and containment space for bone chips
   e. a void formed in said cutting head extending proximally from and adjacent to said cutting edge to said neck;
   f. a plurality of teeth extending distally from said cutting edge, each said tooth being having a base, adjacent sides and an apex to define a triangle, said apex defining a cutting point of said tooth, each said tooth being spaced from an adjacent tooth a distance from about one half a tooth width at its base to about one and one half of a tooth width at its base, said cutting point of said teeth defining a kerf that is wider than the thickness of said cutting head.

2. The sagittal surgical saw blade of claim 1 wherein each said tooth is spaced apart a distance of one base width from each said adjacent tooth.

3. The sagittal surgical saw blade of claim 1 wherein each said tooth is spaced apart a distance of one half of one base width from each said adjacent tooth.

4. The sagittal surgical saw blade of claim 1 wherein each said tooth is spaced apart a distance of one and one half of one base width from each adjacent tooth.

5. The sagittal surgical saw blade of claim 1 wherein said void in said cutting head represents about 35% of the area of the distal portion of said blade body.

6. The sagittal surgical saw blade of claim 1 wherein said cutting point of said teeth defines a kerf that is wider than the thickness of said planar blade body.

7. The sagittal surgical saw blade of claim 1 wherein the thickness of at least said cutting head is less than the thickness of said cutting edge and said teeth.

8. The sagittal surgical saw blade of claim 1 wherein the oscillation path of a tooth overlaps the oscillation path of an adjacent tooth during a cutting operation.

9. The sagittal surgical saw blade of claim 1 wherein said spacing between adjacent teeth is such as to not exceed spacing that allows the oscillation path of a tooth to overlap the oscillation path of an adjacent tooth during a cutting operation.

10. A surgical saw blade comprising a planar blade body having side edges and opposed proximal and distal end edges, upper and lower surfaces, opposed proximal and distal end portions and a longitudinal axis extending between said proximal and distal end edges, said proximal end portion adapted for attachment of said blade body to an oscillatory drive mechanism, said side edges at said distal end portion of said blade body sloping distally inwardly towards said longitudinal axis of said blade body to form a neck and then outwardly to form left and right shoulders in said blade body, a cutting head having a distal end edge being formed by said side edges sloping distally outwardly from said neck to said distal end edge, said distal end edge forming the cutting edge of said blade body, said cutting edge defining teeth, each said tooth having a base, adjacent sides and an apex to define a triangle, each said tooth being spaced from an adjacent tooth a distance equivalent to one half to one and one half of said base, said apex of each tooth being offset from the apex of an adjacent tooth to define a kerf greater than the thickness of said planar body and said side edges of said planar body extending between said left and right shoulders and said cutting edge define left and right collection and containment spaces for cutting chips.

\* \* \* \* \*